(12) United States Patent
Cummings et al.

(10) Patent No.: US 8,951,807 B2
(45) Date of Patent: Feb. 10, 2015

(54) SURFACE NEUTRALIZATION OF APATITE

(75) Inventors: Larry J. Cummings, Pleasant Hill, CA (US); Mark A. Snyder, Oakland, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 0 days.

(21) Appl. No.: 13/006,022

(22) Filed: Jan. 13, 2011

(65) Prior Publication Data

US 2011/0178276 A1 Jul. 21, 2011

Related U.S. Application Data

(60) Provisional application No. 61/295,499, filed on Jan. 15, 2010.

(51) Int. Cl.
| | | |
|---|---|---|
| C07K 1/14 | (2006.01) | |
| G01N 33/538 | (2006.01) | |
| B01D 15/38 | (2006.01) | |
| B01D 15/42 | (2006.01) | |
| B01J 20/04 | (2006.01) | |
| B01J 20/281 | (2006.01) | |
| B01J 20/282 | (2006.01) | |

(52) U.S. Cl.
CPC .......... *B01D 15/3847* (2013.01); *B01D 15/424* (2013.01); *B01J 20/048* (2013.01); *B01J 20/281* (2013.01); *B01J 20/282* (2013.01)
USPC ............ 436/541; 530/344; 530/412; 530/415

(58) Field of Classification Search
CPC ............ B01D 15/203; B01D 15/3847; B01D 15/424; B01J 20/048; B01J 20/281; B01J 20/282
See application file for complete search history.

(56) References Cited

U.S. PATENT DOCUMENTS

| | | | |
|---|---|---|---|
| 3,737,516 A | 6/1973 | Jenner | |
| 4,053,561 A | 10/1977 | Irani | |
| 4,859,342 A | 8/1989 | Shirasawa et al. | |
| 5,332,503 A | 7/1994 | Lee et al. | |
| 5,744,587 A | 4/1998 | Alaska et al. | |
| 5,783,217 A | 7/1998 | Lee et al. | |
| 6,602,697 B1 | 8/2003 | Cook, III | |
| 7,476,722 B2 | 1/2009 | Vedantham et al. | |
| 2003/0166869 A1 | 9/2003 | Vedantham et al. | |
| 2004/0265298 A1 | 12/2004 | Lin | |
| 2005/0107594 A1 | 5/2005 | Sun et al. | |
| 2006/0246544 A1 | 11/2006 | Kang et al. | |
| 2009/0047723 A1 | 2/2009 | Jensen et al. | |
| 2009/0186396 A1 | 7/2009 | Gagnon | |
| 2009/0187005 A1 | 7/2009 | Gagnon | |
| 2009/0264651 A1 | 10/2009 | Daly | |
| 2009/0318674 A1 | 12/2009 | Gagnon | |
| 2010/0113751 A1 | 5/2010 | Sun et al. | |

FOREIGN PATENT DOCUMENTS

| | | |
|---|---|---|
| EP | 0256836 A1 | 2/1988 |
| EP | 1081221 A1 | 3/2001 |
| EP | 2138505 B1 | 8/2014 |
| WO | WO 03/059935 A2 | 7/2003 |
| WO | WO 2006/099308 A2 | 9/2006 |
| WO | 2009/017491 A1 | 2/2009 |

OTHER PUBLICATIONS

Gorbunoff et al.; "The interaction of proteins with hydroxyapatite—I. Role of protein charge and structure"; 1984, *Analytical Biochemistry*, vol. 136, No. 2, pp. 425-432.
International Search Report and Written Opinion from PCT/US2012/023512, dated May 10, 2012.
The International Search Report from PCT/US2011/021158, dated Mar. 17, 2011.
The International Search Report from PCT/US2011/048082, dated Mar. 20, 2012.
U.S. Appl. No. 13/205,354, filed Aug. 8, 2011 (26 pages).
U.S. Appl. No. 13/363,670, filed Feb. 1, 2012 (14 pages).
U.S. Appl. No. 13/891,502, filed May 10, 2013 (30 pages).
Office Action from U.S. Appl. No. 13/363,670, dated Mar. 11, 2013.
Office Action from U.S. Appl. No. 13/363,670, dated Sep. 21, 2012.
Britsch, "Purification of Flavanone 3 beta-Hydroxylase from *Petunia hybrida*: Antibody preparation and Characterization of a Chemogenetically Defined Mutant", *Archives of Biochemistry and Biophysics*, 276(2):348-354 (1990).
Extended European Search Report dated Jul. 18, 2014 for EP Application No. 12742721.9, 6 pages.
Extended European Search Report dated Jul. 21, 2014 for EP Application No. 11733384.9, 7 pages.

*Primary Examiner* — Shafiqul Haq
(74) *Attorney, Agent, or Firm* — Kilpatrick Townsend & Stockton LLP

(57) ABSTRACT

The present invention discloses methods of neutralizing apatite surfaces, for example during chromatography and before protein elution.

20 Claims, No Drawings

SURFACE NEUTRALIZATION OF APATITE

CROSS-REFERENCE TO RELATED PATENT APPLICATIONS

The present patent application claims benefit of priority to U.S. Provisional Patent Application No. 61/295,499, filed Jan. 15, 2010, which is incorporated by reference for all purposes.

BACKGROUND OF THE INVENTION

Hydroxyapatite and fluorapatite, among other apatite solid supports, are used for purification of a wide variety of biomolecules, including proteins, carbohydrates, polynucleotides, and viral particles.

BRIEF SUMMARY OF THE INVENTION

The present invention provides methods for purifying a target molecule in a sample. In some embodiments, the method comprises,
(a) contacting a sample comprising the target molecule to an apatite solid surface thereby adsorbing the target molecule to the solid surface;
(b) contacting the solid surface comprising the adsorbed target molecule with a solution comprising a concentration of:
  (i) a basic amino compound and alkali metal ion or alkali earth ion; or
  (ii) a sulphonated amine compound and alkali metal ion or alkali earth ion,
sufficient to neutralize the apatite solid surface wherein the solution has a sufficiently low ionic strength such that the target molecule remains adsorbed to the solid support; and
(c) eluting the target molecule from the solid support by contacting the solid support with a solution different from the solution in step (b), thereby purifying the molecule in a sample.

In some embodiments, the method comprises:
(a) contacting a sample comprising the target molecule to an apatite solid surface thereby adsorbing the target molecule to the solid surface;
(b) contacting the solid surface comprising the adsorbed target molecule with a solution comprising:
  (i) a basic amino compound and an alkali metal ion; or
  (ii) a sulphonated amine compound and an alkali metal ion,
of sufficient volume and concentration to neutralize the apatite solid surface wherein the solution has a sufficiently low ionic strength such that the target molecule remains adsorbed to the solid support; and
(c) eluting the target molecule from the solid support by contacting the solid support with a solution of different composition from the solution in step (b), thereby purifying the target molecule in a sample.

In some embodiments, the alkali metal ion is selected from lithium, sodium, or potassium.

In some embodiments, the alkali earth ion is selected from magnesium and calcium.

In some embodiments, the apatite is selected from the group consisting of hydroxyapatite and fluorapatite.

In some embodiments, the target molecule is a protein. In some embodiments, the target protein is an antibody.

In some embodiments, the solution in step (b) has a pH between 6.5 and 9.0 or between 7-8.5, or between 7.5-9.0.

In some embodiments, the solution has 100 mM, 80 mM, 60 mM or less of alkali metal ion or alkali earth ion.

In some embodiments, the method further comprises one or more additional wash steps between any of the foregoing steps (a) and (b) or any of the foregoing steps (b) and (c). In some embodiments, the one or more additional wash steps remove at least one component of the sample from the solid surface while substantially retaining the target molecule on the solid support. In some embodiments, the component washed from the support is selected from at least one of the group consisting of endotoxin, host cell protein, aggregated target protein or other aggregates, neutral lipids, charged lipids, polysaccharides, precipitating agents, non-target small molecules and aggregated target protein.

In some embodiments, the solution comprises a sulphonated amine compound. In some embodiments, the sulphonated amine compound is selected from PIPES, MES, MOPS, ACES, MOPSO, and HEPES. In some embodiments, the concentration of the sulphonated amine compound is between 5-500 mM. In some embodiments, the concentration of the sulphonated amine compound is between 5-100 mM. In some embodiments, the concentration of the sulphonated amine compound is between 5-50 mM.

In some embodiments, the solution comprises the amino compound. In some embodiments, the amino compound is selected from the group consisting of tris(hydroxymethyl) aminomethane (e.g., Tris™), lysine, histidine, arginine, and imidazole. In some embodiments, the concentration of the amino compound is between 5-500 mM. In some embodiments, the concentration of the amino compound is between 5-100 mM. In some embodiments, the concentration of the amino compound is between 5-50 mM.

In some embodiments, the solid support is a column and the step (b) comprises contacting the solid surface with at least one, two, three, four, five, six, seven, eight, or more column volumes of the solution.

In some embodiments, the apatite is ceramic hydroxyapatite or ceramic fluorapatite. In some embodiments, the apatite is a non-ceramic apatite.

DEFINITIONS

"Neutralizing the solid apatite surface" refers to treating the surface of the apatite surface such that the solid surface does not contain sufficient hydronium ions to significantly affect (i.e., cause a greater than 0.2 acidic pH shift of) the pH of a subsequent elution buffer.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified fauns such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

An "apatite solid surface" include fused nanocrystals (ceramic apatite), microcrystals, or compounded microcrystals. Ceramic apatites include, but not limited to, ceramic hydroxyapatite (e.g., CHT™) or ceramic fluorapatite. Ceramic apatites are a form of apatite minerals in which nanocrystals are agglomerated into particles and fused at high temperature to create stable ceramic microspheres suitable for chromatography applications. Compounded microcrystals include but are not limited to HA Ultragel® (Pall Corp.).

Microcrystals include but are not limited to Bio-Gel HTP, Bio-Gel® HT, DNA-Grade HT (Bio-Rad) and Hypatite C (Clarkson Chromatography).

"Hydroxyapatite" refers to a mixed mode support comprising an insoluble hydroxylated mineral of calcium phosphate with the structural formula $Ca_{10}(PO_4)_6(OH)_2$. Its dominant modes of interaction are phosphoryl cation exchange and calcium metal affinity. Hydroxapatite is commercially available in various forms, including but not limited to ceramic, crystalline and composite forms. Composite forms contain hydroxyapatite microcrystals entrapped within the pores of agarose or other beads.

"Fluorapatite" refers to a mixed mode support comprising an insoluble fluoridated mineral of calcium phosphate with the structural formula $Ca_{10}(PO_4)_6F_2$. Its dominant modes of interaction are phosphoryl cation exchange and calcium metal affinity. Fluorapatite is commercially available in various forms, including but not limited to ceramic and crystalline composite forms.

"Sample" refers to any composition having a target molecule or particle of interest. A sample can be unpurified or partially purified. Samples can include samples of biological origin, including but not limited to blood, or blood parts (including but not limited to serum), urine, saliva, feces, as well as tissues.

An "alkali earth ion" refers to any cation elements in Group IIA of the periodic table, including, e.g., beryllium (Be), magnesium (Mg), calcium (Ca), strontium (Sr), barium (Ba) and radium (Ra). Practitioners will recognize that Mg and Ca are most commonly used in chromatography. An alkali earth ion can be delivered to a solution, for example, as a salt with one or more ionic counter ion(s) (e.g., $CaCl_2$, etc.).

An "alkali metal ion" refers to any cation elements in Group I of the periodic table, including, e.g., lithium (Li), sodium (Na), potassium (K), rubidium (Rb), cesium (Cs), and francium (Fr). Practitioners will recognize that Na and K are most commonly used in chromatography. An alkali metal ion can be delivered to a solution as a salt with one or more ionic counter ion(s) (e.g., KOH, NaOH, NaCl, etc.).

DETAILED DESCRIPTION

I. Introduction

The present invention is based, in part, on the discovery that a neutralization solution comprising an amino compound or a sulfonate amine compound, in combination with an alkali metal ion, and optionally also an alkali earth ion, is effective in neutralizing apatite solid surfaces used for chromatography purification, without significantly eluting the target molecule to be eluted at a later stage. The present application provides for methods of adsorbing a target molecule (e.g., protein or other molecule) to an apatite solid surface, neutralizing the apatite surface as described herein with a neutralization solution, and then eluting the target molecule with a separate solution or a solution having a different composition than the neutralization solution.

The neutralization solution can comprise an amino compound or a sulfonate amine, or both. Under appropriate conditions, alkali earth or alkali metal ions displace hydronium ions on the apatite surface and the amino or sulfonate amine compounds act as hydronium ion acceptors, thereby removing the hydronium ions without harming the apatite solid surface, substantially changing the pH of the solution, or substantially eluting the target compound to be purified. Said another way, the invention provides for neutralization by contacting with a buffer under conditions so that the buffer that can exchange a cation for a hydronium ion on the apatite surface, wherein the hydronium ion is sequestered by another component of the neutralization solution (i.e., an amino compound or a sulphonated amine compound). Following neutralization of the surface, a different solution is used to elute the target molecule.

II. Hydronium Ion

Elution of target proteins or other target molecules from apatite surfaces can create a significant release of hydronium ions, which can be harmful to the target molecule and/or the apatite solid surface, thereby reducing one's ability to re-use the apatite material. The inventors have discovered that following adsorption of the target molecule onto the apatite solid surface, one can remove and neutralize hydronium ions on the apatite by contacting the apatite surface with an amino compound or sulfonate amine compound, in combination with alkali earth or alkali metal ions, at a sufficiently low concentration and ionic strength to avoid substantially eluting the target molecule.

A. General

Initially, the sample containing the target molecule is adsorbed to the apatite surface as is known in the chromatography arts. Optionally, the apatite surface is previously sanitized and/or equilibrated prior to adsorption of the target to the surface. Optionally, one or more wash steps can be performed before or after the neutralization step. In some embodiments, the neutralization step itself also functions as a wash step, i.e., substantially removing at least one component of the sample from the solid support. Wash steps can be designed to remove one or more non-target components of the sample while retaining the target protein. Alternatively, or in addition, further wash steps can be employed to desorb one or more of endotoxin, host cell proteins, aggregates of target protein or other aggregates, neutral lipids, polysaccharides, small molecules, charged lipids, or other non-target molecules such as residual precipitating agents from a prior purification step while substantially retaining (e.g., retaining at least 80%, 90%, 95% or more) target proteins on the solid support during the wash.

The neutralization comprises contacting the apatite surface comprising the adsorbed target with a solution comprising a buffer that can buffer in the range of 6.5-9.0 (including but not limited to an amino compound and/or a sulphonate amine compound) at an appropriate pH (e.g., pH 6.5-9.0) and concentration (e.g., 5-500 mM or 5-100 mM) to act as a hydronium ion acceptor, as further discussed below. In combination, sufficient alkali earth ions (and also optionally alkali metal ions) are contacted to the apatite surface to displace hydronium ions on the apatite surface. However, the concentration of the buffer (e.g., amino compound and/or a sulphonate amine compound) as well as the concentration of cation(s) are sufficiently low to prevent elution of the target molecule adsorbed to the apatite. Such concentrations can vary depending on the target molecule adsorbed to the apatite, but in some embodiments are less than 500 mM, or less than 100 mM or less than 50 mM, e.g., 5-100 mM, or 10-50 mM, or 10-30 mM. Further, the pH of the neutralization solution can be adjusted such that the buffer acts as hydronium ion acceptors without significantly eluting the target molecule from the apatite surface.

Neutralization of the apatite surface can be readily measured. For example, one can monitor the pH of the chromatography effluent during elution of the target molecule. A neutral apatite surface will result in a pH change of no more than 0.1 or 0.2 between the input and effluent following neutralization. For example, if the pH of the elution buffer is input at 7.0, the effluent would not drop to less than 6.8 during elution if the surface were neutralized. Alternatively, one can monitor calcium ions in the effluent to determine whether the surface is neutralized. In the presence of released free hydronium ion, apatite releases calcium. Thus, the presence of more calcium in the effluent than what was in the input buffer indicates that the surface has not been neutralized.

Following neutralization, and optional wash steps, the target molecule is eluted. Elution is achieved, for example, by changing the pH and/or salt conditions compared to the neutralization conditions or otherwise changing the composition of the wash. In some embodiments, elution is achieved by changing the salt conditions in the liquid phase. For example, in some embodiments, the salt and/or conductivity of the liquid phase is increased (linearly or step-wise) to a point that which the target elutes. In some embodiments, the buffer in the neutralization solution is substantially removed prior to elution. In some embodiments, elution of the target is initiated by contacting the apatite surface with an elution solution that lacks the buffer in the neutralization solution. It will be appreciated that residual buffer from the neutralization step may be present but if so, will be at increasingly reduced concentration during elution due to absence of the buffer in the elution solution.

B. Exemplary Buffer: Amino Compounds

Amino compounds refer to compounds that have an amino moiety, i.e., an —$NH_2$ moiety. As demonstrated in the examples, a wide range of amino compounds can be used as hydronium ion acceptors, thereby neutralizing the ions. Exemplary amino compounds include, but are not limited to histidine, arginine, Tris (($HOCH_2)_3CNH_2$), and lysine. In some embodiments, arginine concentrations are from 5-100 mM, e.g., 5-50, 5-30, or 10-30 mM. The pH of the arginine solution in some embodiments is 7-9, e.g., 7.5-8.5.

In some embodiments, the amino compound is histidine. As noted in the examples, histidine is effective in neutralizing hydronium ions on apatite surfaces. In some embodiments, the histidine solution has a pH of between 6.5-9, or 7-9, or 8.1-9, e.g., 8.2-8.6, and a concentrations of 5-500 mM, e.g., 5-100 mM, 5-50, or 5-30 mM.

In some embodiments, the amino compound is Tris. In some embodiments, the Tris concentration is between 5-50 mM, e.g., 5-30 mM, and is sufficiently low to avoid significant target elution. As shown in the examples, in combination, an amount of sodium ions can be used to displace hydronium ions from the apatite surface. However, as noted elsewhere other alkali earth cations can also be used. In some embodiments, the pH is between 6.5-9, e.g., between 7.5-8.5.

In view of the disclosures herein, it will be appreciated that other amino compounds can also be used in a neutralization solutions according to the methods of the invention to accept hydronium ions from the solid surface. In some embodiments, the neutralization solution contains two or more different amino compounds as hydronium acceptors.

C. Exemplary Buffer: Sulphonated Amines

Sulphonated amine compounds refer to a chemical compound that comprises a sulfoxide moiety and an amine. The amine can be a primary, secondary, tertiary, or quaternary amine. The sulfoxide moiety can, but does not have to be, directly linked to the amine.

As shown in the Example, when used at sufficiently high pH and in sufficient amount, piperazine disuphonate (PIPES) is an effective neutralizer. In some embodiments, the concentration of PIPES is between 5-500 mM, e.g., 5-100 mM, 5-50 mM. As shown in the examples, a source of sodium ions can be used to displace hydronium ions from the apatite surface. In some embodiments, the sodium concentration is 1-20 mM, e.g., 1-10 mM. However, as noted elsewhere other alkali earth or alkali metal cations can also be used. In some embodiments, the pH is between 7-9, e.g., between 7.5-8.5.

In some embodiments, the sulphonated amine compound is MES (2-(N-morpholino)ethanesulfonic acid) or HEPES (4-(2-hydroxyethyl)-1-piperazineethanesulfonic acid). In some embodiments, the concentration of MES or HEPES is between 5-100 mM, e.g., 5-50 mM. In addition, a source of sodium ions can be used to displace hydronium ions from the apatite surface. In some embodiments, the sodium concentration is 1-100 mM, e.g., 10-80, e.g., 10-50 mM. However, as noted elsewhere other alkali earth or alkali metal cations can also be used, in the same concentrations as listed above for sodium. In some embodiments, the pH is between 6.5-9, e.g., between 7.5-8.5.

In some embodiments, the sulphonated amine compounds are one of those described in US Patent Publication No 2009/0264651, including but not limited to those described in claim 12 or 13 of the publication.

In some embodiments, the sulphonated amine compound is ACES (N-(2-Acetamido)-2-aminoethanesulfonic acid), MOPS (3-(N-morpholino)propanesulfonic acid), or MOPSO (3-(N-Morpholino)-2-hydroxypropanesulfonic acid), optionally under conditions such as those described above for other sulphonated amines.

In view of the disclosures herein, it will be appreciated that other sulphonated amine compounds can also be used in a neutralization solution according to the methods of the invention to accept hydronium ions from the solid surface. In some embodiments, the neutralization solution contains two or more different sulphonated amine compounds as hydronium acceptors. In some embodiments, the neutralization solution contains one or more amino compounds and one or more sulphonated amine compounds.

D. Alkali Earth Ions and Alkalai Metal Ions

Alkali metal cations (and optionally also alkali earth cations) can be used to displace hydronium ions from the apatite surface. The hydronium ion is subsequently sequestered by another component of the neutralization buffer. The alkali metal ions and/or the alkali earth ions can initially form a salt with the amino compound or the sulfonate amine compound or alternatively can be added separately to the neutralization solution, e.g., as a salt with another counter ion (e.g., —OH, —Cl, etc.).

III. Apatites

Those of skill will appreciate that a number of types of apatite solid surfaces can be used in the invention. Commercial examples of ceramic hydroxyapatite include, but are not limited to CHT Type I and CHT Type II. Commercial examples of ceramic fluorapatite include, but are not limited to CFT™ Type I and CFT Type II. Unless specified, ceramic hydroxyapatite and ceramic fluorapatite refer to roughly spherical porous particles of any average diameter, including but not limited to about 10, 20, 40, and 80 microns. The choice of hydroxyapatite or fluorapatite, the type, and average particle diameter can be determined by the skilled artisan. Other non-ceramic types of apatite solid surfaces (including those sold as "gels") can also be used according of the invention. Examples of non-ceramic solid apatites include but are not limited to compounded microcrystals (e.g., HA Ultragel® (Pall Corp.)) and microcrystals (e.g., Bio-Gel HTP, Bio-Gel® HT, DNA-Grade HT (Bio-Rad) and Hypatite C(Clarkson Chromatography)).

In preparation for contacting the sample with the apatite support, the chemical environment inside the column is typically equilibrated. This can be accomplished, for example, by flowing an equilibration buffer through the column to establish the appropriate pH; conductivity; identity, molecular weight, and other pertinent variables.

In some embodiments, the sample preparation is also equilibrated to conditions compatible with the column equilibration buffer. In some embodiments, this involves adjusting the pH of the sample preparation prior to loading.

In some embodiments, after the column and sample preparation is equilibrated, the sample preparation is contacted with the column. The sample preparation can be applied at a linear flow velocity in the range of, for example, about 50-600 cm/hr. Appropriate flow velocity can be determined by the skilled artisan.

In some embodiments, the invention is practiced in a packed bed column, a fluidized/expanded bed column and/or a batch operation where the support is mixed with the sample preparation for a certain time. In some embodiments, an apatite support is packed in a column. In some embodiments, the apatite support is packed in a column of at least 5 mm internal diameter and a height of at least 25 mm.

Another embodiment employs the apatite support, packed in a column of any dimension to support preparative applications. Column diameter may range from less than 1 cm to more than 1 meter, and column height may range from less than 1 cm to more than 30 cm depending on the requirements of a particular application. Appropriate column dimensions can be determined by the skilled artisan.

After use, the mixed mode column can optionally be cleaned, sanitized, and stored in an appropriate agent, and optionally, re-used. Indeed, one benefit of the neutralization solution of the present invention is that degradation of an apatite column can be avoided or delayed. Thus, in some embodiments, one can use the column for ten or more times, e.g., more than 20, more than 30, more than 40 or more than 50 cycles of purification.

IV. Uses

The methods of the invention can be used to purify essentially any target molecule in a complex sample. In some embodiments, the target molecule to be purified is a component of a biological sample. Examples of such components include but are not limited to proteins, lipids, sugars, carbohydrates, viral particles, amino acids, nucleic acids, and can include combinations thereof, e.g., a lipidated or glycosylated protein, or mixtures thereof. In some embodiments, samples to which the method is applied include unpurified or partially purified biomolecules from natural, synthetic, or recombinant sources. Unpurified samples can be derived from, e.g., plasma, serum, ascites fluid, milk, plant extracts, bacterial lysates, yeast lysates, or conditioned cell culture media. In some embodiments, partially purified samples come from unpurified preparations that have been processed by at least one chromatography, ultrafiltration, precipitation, other fractionation step, or any combination thereof. An exemplary target molecule is an antibody (including but not limited to a monoclonal antibody and/or antibody fragments) or other peptide or polypeptide. The chromatography step or steps can employ any method, including but not limited to size exclusion, affinity, anion exchange, cation exchange, protein A affinity, hydrophobic interaction, immobilized metal affinity chromatography, or mixed-mode chromatography. The precipitation step or steps can include, for example, salt or PEG precipitation, or precipitation with organic acids, organic bases, or other agents. Other fractionation steps can include but are not limited to crystallization, liquid:liquid partitioning, or membrane filtration. Ultrafiltration can include direct concentration of the sample and/or diafiltration.

EXAMPLES

The following examples are offered to illustrate, but not to limit the claimed invention.

Various apatite chromatography supports can be used for protein purification. However, adsorption and subsequent elution of proteins from apatite supports can generate strong acids, including hydrochloric and nitric acids, which have been attributed to chemical degradation of the supports, limiting the re-use of the supports.

We have discovered that solutions comprising buffering compounds (basic amino or amino sulphonates compounds) and alkali metal or alkali earth compounds neutralize the surface of apatite chromatography supports without significantly eluting the adsorbed protein. Thus, during protein elution, fewer hydronium ions are released from the hydroxyapatite surface, thereby generating milder conditions than would otherwise occur, avoiding the generation of strong acids and the subsequent degradation of the apatite support.

Example 1

Post load surface neutralization was determined as follows. A hydroxyapatite (CHT Type I) column was sanitized with Sanitization solution (1 M NaOH/1 M NaCl), rinsed briefly with Equilibration buffer (5 mM sodium phosphate/0.1 M NaCl, at pH 6.5), conditioned with Regeneration buffer (0.4 M sodium phosphate, pH 7.0), rinsed with 20 volumes of Equilibration buffer (10 column volumes to equilibrate, 8 column volumes as simulated protein load and 2 column volumes for post load rinsing) then contacted with 1.0 column volume of post-load solution comprising 0.1 M arginine, pH 11 We found that the 1.0 column volume post-load step quickly shifted the pH to greater than 8. The column was then eluted with Elution buffer (0.55 M NaCl/5 mM sodium phosphate at pH 6.5). The calcium ion content of the Elution buffer effluent was negative indicating that the 0.1 M arginine at pH 11 was sufficient to neutralize the apatite surface.

Example 2

The same conditions as described were repeated, but this time with only a 0.8 post-load column volume. The basic pH shift was minimized as a result of the reduced post-load column volume. This and the above experiment demonstrated that arginine was effective in neutralizing the surface of the CHT column.

Example 3

We then tested the effect of the arginine post-load solution on an adsorbed protein. Unless specified differently, in each of the experiments described below, the protein was eluted with Elution buffer (0.55 M NaCl, 5 mM sodium phosphate at pH 6.5) following the various post-load solutions discussed. Bovine IgG was initially adsorbed to a CHT column, the column was equilibrated with 5 mM PB, 0.1 NaCl pH 6.5, and subsequently contacted with 0.8 column volumes of 0.1 M arginine, pH 11, as a post-load treatment. The bovine IgG was not retained on the column, most likely because the high pH of the arginine solution, allowing it to displace the protein by cation exchange.

Example 4

0.1 M arginine citrate, pH 8 was used as a post-load solution. Most but not all of the bovine IgG was eluted under this condition, indicating that the lower pH reduced the ability of arginine to act as a cation exchanger, and to displace the IgG.

This was particularly interesting as we found that use of 120 mM citrate pH 8.3, while an effective surface neutralizer, dissolved the CHT column.

Example 5

The concentration of arginine citrate pH 8.0 in the post-load was reduced to 20 mM. This post-load concentration greatly increased the amount of protein retained during the post-load step, with greater than 90% of the IgG retained in the column following a 4.67 column volume post-load step.

Example 6

We determined that piperazine disulphonate (PIPES), when applied at a sufficiently high pH, and in sufficient amount as a post-load treatment, is an effective column neutralizer. For example, 25 mM PIPES/5 mM sodium phosphate/25 mM NaCl/4 ppm calcium at pH 8.25 was effective at neutralizing the column when at least 6 column volumes were used as a post-load treatment. The Elution buffer effluent contained less than 4 ppm calcium ion. Ordinarily, if the surface were not neutralized, the calcium ion content would be 52 ppm.

Example 7

A variety of alternative post-load solutions were tried. Neither 4 mM trisodium phosphate, pH 8.1; 20 mM sodium bicarbonate at pH 8.1 or 9.0; 50 mM MES pH 7.13; 20 mM histidine, pH 8.0; nor 50 mM sodium acetate, pH 7.51 were effective in neutralizing the column. However, 25 mM histidine, 25 mM NaCl, 5 mM phosphate at pH of 8.4 was effective at neutralization. Similarly, 20 mM MES, 25 mM NaCl, 5 mM phosphate at pH of 8.4 was effective at neutralization.

Example 8

We determined that Tris, when applied at a sufficiently high pH, and in sufficient amount as a post-load treatment, is an effective column neutralizer without displacing the bound protein. For example, relatively high concentrations of Tris (e.g., 50 mM) at pH 9.03 or 10.3 was sufficient to neutralize the column, but resulted in significant elution of IgG. However, 25 mM Tris, 25 mM NaCl pH 8.4 was effective at neutralizing the column while not eluting bound IgG when 6 column volumes were used as a post-load treatment (1.9 column volumes was not sufficient to neutralize the column). Thus, a relatively low concentration of Tris, when applied over a number of column volumes, is effective in neutralizing the column surface without significant (e.g., less than 10% or less than 5%) elution of the bound protein.

Another protein, human serum albumin (HSA), which has a pI of 5.9-6.4 is an example of a protein preferentially desorbed by the post-load treatment. In these experiments, HSA and IgG were adsorbed to the column and then washed in a post-load treatment in 4 column volumes of 25 mM Tris-HCl, 25 mM NaCl pH 8.4. The post-load treatment neutralized the surface of the column and desorbed HSA but IgG was retained. Thus, the post-load washes are effective in neutralizing the column surface while eluting HSA, but not the IgG target protein.

Accordingly, in some embodiments of the invention, following absorption of protein to an apatite column, a solution of one or more basic amino compounds or sulphonated amine compounds in the presence of less than 100 mM alkali metal (e.g., lithium, sodium, etc.) or alkali earth (calcium, magnesium, etc.) at a pH of between 6.5-9.0 is used to neutralize the column surface prior to elution of the target protein. In some embodiments, the proteins are initially adsorbed to the solid surface in a low ionic strength solution at between pH 6.5 and 7.4, though those of skill in the art will recognize that other conditions can also be employed for protein adsorption.

The following table summarizes neutralization data from a number of different buffer preparations:

| Wash Buffer | pH | CV | pH Wash End | pH NaCl Eluate | Calcium ppm | pH NaCl Eluent | Result |
|---|---|---|---|---|---|---|---|
| 20 mM ACES, 25 mM NaCl, 5 mM NaPO4 | 7.50 | 8.0 | 7.58 | 6.66 | 15 | 6.50 | Passed |
| 25 mM Arginine, 25 mM NaCl, 5 mM NaPO4 | 8.00 | 8.0 | 7.40 | 6.85 | 12 | 6.50 | Passed |
| 20 mM HEPES, 25 mM NaCl, 5 mM NaPO4 | 7.50 | 8.0 | 7.44 | 6.50 | 25 | 6.50 | Passed |
| 20 mM Histidine, 5 mM NaPO4 | 7.75 | 3.5 | 7.72 | 6.23-5.91 | 46-251 | 6.23 | Failed |
| 25 mM Histidine, 25 mM NaCl | 6.50 | 10.0 | 6.50 | 5.80 | Unknown | 6.50 | Failed |
| 25 mM Histidine, 25 mM NaCl | 6.80 | 10.0 | 6.80 | 5.90 | Unknown | 6.50 | Failed |
| 25 mM Histidine, 25 mM NaCl, 5 mM NaPO4 | 8.40 | 8.0 | 8.19 | 7.21 | 9 | 6.50 | Passed |
| 25 mM Histidine, 25 mM NaCl, 5 mM NaPO4 | 7.75 | 8.0 | 7.58 | 6.59 | 22 | 6.50 | Passed |
| 25 mM Lysine, 25 mM NaCl, 5 mM NaPO4 | 8.00 | 8.0 | 7.80 | 6.76 | 11 | 6.50 | Passed |
| 50 mM MES, 5 mM NaPO4 | 7.13 | 3.5 | 6.99 | 6.35-6.05 | 56-100 | 6.50 | Failed |
| 25 mM MES, 5 mM NaPO4 | 6.55 | 5.7 | 7.98 | 5.6 | 130 | 6.50 | Failed |
| 20 mM MES, 25 mM NaCl, 5 mM NaPO4 | 8.40 | 8.0 | 7.75 | 6.66 | 14 | 6.50 | Passed |
| 20 mM MES, 25 mM NaCl, 5 mM NaPO4 | 7.75 | 8.0 | 7.45 | 6.76 | 12 | 6.50 | Passed |
| 20 mM MOPS, 25 mM NaCl, 5 mM NaPO4 | 7.50 | 8.0 | 7.55 | 6.52 | 18 | 6.50 | Passed |
| 25 mM PIPES, 25 mM NaCl, 5 mM NaPO4, 0.25 mM CaCl2 | 8.25 | 8.0 | 8.00 | 7.00 | Unknown | 6.60 | Passed |
| 12.5 mM PIPES, 25 mM NaCl, 5 mM NaPO4, 0.25 mM CaCl2 | 7.15 | 8.0 | 7.14 | 6.21 | 256 | 6.60 | Failed |
| 12.5 mM PIPES, 25 mM NaCl, 5 mM NaPO4, 0.25 mM CaCl2 | 7.75 | 8.0 | 7.57 | 6.74 | 12 | 6.60 | Passed |
| 12.5 mM PIPES, 25 mM NaCl, 5 mM NaPO4, 0.25 mM CaCl2 | 7.75 | 8.0 | 7.57 | 6.74 | 12 | 6.60 | Passed |
| 25 mM Tris, 25 mM NaCl, 5 mM NaPO4 | 8.40 | 4.0 | 7.75 | 6.55 | Unknown | 6.50 | Failed |
| 25 mM Tris, 25 mM NaCl, 5 mM NaPO4 | 8.40 | 6.0 | 8.00 | 6.52 | 10 | 6.50 | Passed |
| 25 mM Tris, 25 mM NaCl, 5 mM NaPO4 | 8.00 | 8.0 | 7.82 | 6.94 | 10 | 6.50 | Passed |
| 25 mM Tris, 25 mM NaCl, 5 mM NaPO4 | 8.37 | 4.0 | 7.04 | 6.40 | 35-60 | 6.49 | Failed |
| 25 mM Tris, 25 mM NaCl, 5 mM NaPO4 | 8.25 | 8.0 | 7.42 | 7.27-6.50 | 20 | 6.50 | Passed |
| 25 mM Tris, 25 mM NaCl, 5 mM NaPO4, 4pm Ca | 8.40 | 8.0 | 7.51 | 7.15-7.43 | 10 | 6.50 | Passed |

-continued

| Wash Buffer | pH | CV | pH Wash End | pH NaCl Eluate | Calcium ppm | pH NaCl Eluent | Result |
|---|---|---|---|---|---|---|---|
| 25 mM Tris, 25 mM NaCl, 5 mM NaPO4 | 8.40 | 8.0 | 8.00 | 6.80 | Unknown | 6.50 | Passed |
| 20 mM Tris, 20 mM Arginine, 5 mM NaPO4 | 7.40 | 6.0 | 7.40 | 5.98 | 92 | 6.50 | Failed |

Passed = Neutralized
Failed: indicates significant calcium leaching or column mass loss. Failed runs could indicate insufficient volume of neutralizing wash buffer, pH too low, lack of NaCl in the wash buffer, or a combination thereof It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for purifying a target molecule in a sample, the method comprising,
    (a) equilibrating an apatite solid surface with a buffer composition suitable to adsorb the target molecule on the apatite solid surface and then contacting the sample comprising the target molecule to the apatite solid surface thereby adsorbing the target molecule to the solid surface;
    (b) after step (a), contacting the solid surface comprising the adsorbed target molecule with a solution having a pH of 7.5-9.0, the solution comprising:
        (i) a basic amino compound and an alkali metal ion; or
        (ii) a sulphonated amine compound and an alkali metal ion,
    of sufficient volume and concentration to neutralize the apatite solid surface wherein the solution has a sufficiently low ionic strength such that the target molecule remains adsorbed to the solid support, wherein the buffer composition in step (a) is of different composition from the solution in step (b); and
    (c) after step (b), eluting the target molecule from the neutralized solid support by contacting the solid support with a solution of different composition from the solution in step (b), thereby purifying the target molecule in a sample.

2. The method of claim 1, wherein the alkali metal ion is selected from lithium, sodium, or potassium.

3. The method of claim 1, wherein the apatite is selected from the group consisting of hydroxyapatite and fluorapatite.

4. The method of claim 1, wherein the target molecule is a protein.

5. The method of claim 4, wherein the protein is an antibody.

6. The method of claim 1, wherein the solution has 100 mM or less of alkali metal ion.

7. The method of claim 1, further comprising one or more additional wash steps between steps (a) and (b) of claim 1 or between steps (b) and (c) of claim 1.

8. The method of claim 7, wherein the one or more additional wash steps remove at least one component of the sample from the solid surface while substantially retaining the target molecule on the solid support.

9. The method of claim 8, wherein the component is selected from at least one of the group consisting of endotoxin, host cell protein, aggregated target protein or other aggregates, neutral lipids, charged lipids, polysaccharides, precipitating agents, non-target small molecules and aggregated target protein.

10. The method of claim 1, wherein the solution comprises a sulphonated amine compound.

11. The method of claim 10, wherein the sulphonated amine compound is selected from PIPES, MES, MOPS, ACES, MOPSO, and HEPES.

12. The method of claim 10, wherein the concentration of the sulphonated amine compound is between 5-100 mM.

13. The method of claim 10, wherein the concentration of the sulphonated amine compound is between 5-50 mM.

14. The method of claim 1, wherein the solution comprises the basic amino compound.

15. The method of claim 14, wherein the amino compound is selected from the group consisting of tris(hydroxymethyl) aminomethane, lysine, histidine, arginine, and imidazole.

16. The method of claim 1, wherein the solid support is a column and the step (b) comprises contacting the solid surface with at least one column volume of the solution.

17. The method of claim 14, wherein the concentration of the amino compound is between 5-100 mM.

18. The method of claim 14, wherein the concentration of the amino compound is between 5-50 mM.

19. The method of claim 1, wherein the apatite is ceramic hydroxyapatite or ceramic fluorapatite.

20. The method of claim 1, wherein the apatite is a non-ceramic apatite.

* * * * *